(12) United States Patent
Smith

(10) Patent No.: US 7,175,427 B2
(45) Date of Patent: Feb. 13, 2007

(54) VISUALLY SIMULATED TOOTH BRACES

(75) Inventor: Fred R. Smith, O'Hara Township, Allegheny County, PA (US)

(73) Assignee: Ingenious Concepts, Inc., Allison Park, PA (US)

( * ) Notice: Subject to any disclaimer, the term of this patent is extended or adjusted under 35 U.S.C. 154(b) by 228 days.

(21) Appl. No.: 10/919,454

(22) Filed: Aug. 16, 2004

(65) Prior Publication Data

US 2006/0035198 A1    Feb. 16, 2006

(51) Int. Cl.
*A61C 70/00*     (2006.01)
(52) U.S. Cl. .................. 433/9; 433/6; 433/229
(58) Field of Classification Search ........... 433/215, 433/229, 219, 6–24
See application file for complete search history.

(56) References Cited

U.S. PATENT DOCUMENTS

| | | | | |
|---|---|---|---|---|
| 3,813,781 | A | * | 6/1974 | Forgione ................ 433/68 |
| 4,632,880 | A | * | 12/1986 | Lapidus ................ 428/523 |
| 4,741,700 | A | * | 5/1988 | Barabe ................ 433/229 |
| 5,104,320 | A | * | 4/1992 | Stoll ................ 433/206 |
| 5,692,895 | A | | 12/1997 | Farzin-Nia et al. |
| 5,759,039 | A | * | 6/1998 | Kunstadter et al. ........ 433/215 |
| 5,810,593 | A | * | 9/1998 | White et al. ............ 433/206 |
| 5,931,667 | A | * | 8/1999 | Papandreas ............ 433/8 |
| 6,036,949 | A | | 3/2000 | Cohen |
| 6,503,312 | B2 | * | 1/2003 | Altwirth ............ 106/35 |
| 2002/0192617 | A1 | * | 12/2002 | Phan et al. ............ 433/6 |
| 2005/0279378 | A1 | * | 12/2005 | Lorch ................ 132/321 |

OTHER PUBLICATIONS

Halloween Treats for Healthy Teeth, The Citizen News, Oct. 31, 2001.
Tooth Tat-2's, http://webinsi5.website.net/mivastore, printed Oct. 28, 2004.
YUK pack, http://webinsi5.website.net/mivastore, printed Oct. 28, 2004.
X Pack, http://webinsi5.website.net/mivastore, printed Oct. 28, 2004.
LOVE Pack, http://webinsi5.website.net/mivastore, printed Oct. 28, 2004.
FRIENDS Pack, http://webinsi5.website.net/mivastore, printed Oct. 28, 2004.
Wild Smiles Advertisement, American Journal of Orthodontics and Dentofacial Orthopedics, Jun. 2004.

* cited by examiner

*Primary Examiner*—Cary E. O'Connor
(74) *Attorney, Agent, or Firm*—The Webb Law Firm

(57) ABSTRACT

Visually simulated tooth braces include individual visual tooth brace indicia to simulate real functional braces commonly worn by children and adults alike to adjust human teeth. The visually simulated tooth braces allow for children to temporarily wear braces as many of their classmates, friends, and siblings do.

22 Claims, 2 Drawing Sheets

VISUALLY SIMULATED TOOTH BRACES

BACKGROUND OF THE INVENTION

1. Field of the Invention

The present invention relates generally to non-working copies of brace systems for adjusting human teeth, and, in particular, visually simulated tooth brace visual indicia.

2. Description of the Prior Art

In the field of dentistry and orthodontics, braces are used to assist in adjusting the angle and displacement of human teeth. As the technology of manufacturing and applying braces to human teeth develops, the market and class of patients increase accordingly. Both children and adults utilize braces to straighten their teeth for aesthetic reasons.

Children, once despising braces for the appearance when applied, have come to enjoy the myriad of shapes and colors that are now available due to these technological and manufacturing improvements. Originally, in order to reduce the metallic appearance of the braces in the mouth, clear braces, or partially clear braces, were developed. In a further improvement, the use of a phosphorescent or fluorescent pigment applied to the braces was conceived to increase the aesthetic quality of the appearance of a person's braces. See U.S. Pat. No. 5,592,895 to Farrokh et al. This same colorizing technique applied directly to a human tooth has also been developed, as seen in U.S. Pat. No. 6,036,494 to Cohen. In a further cosmetic advance, temporary tattoos have been developed by KidGenics for use on teeth. See www.ToothTat2.com. Indeed, many children now look to the opportunity to wear braces as a right of passage to adulthood. It is therefore an object of the present invention to provide temporary visually simulated braces for children who seek the aesthetic appeal of those who wear braces for teeth adjustment purposes.

SUMMARY OF THE INVENTION

The present invention is a plurality of connected visually simulated indicia for braces on human teeth. The present invention includes an FDA approved substance that temporarily attaches to the user's teeth by the use of a dissolvable FDA approved adhesive. In use, the attaching carrier is attached to the teeth such that the visual indicia are visible to others when the user opens his or her mouth.

The present invention is shaped to simulate functional braces and can be worn for up to four hours or even up to twelve hours. The present invention adaptably molds to the teeth of the user either prior to use or during attachment. The present invention serves no functional purpose for adjusting human teeth.

The present invention, both as to its construction and its method of operation, together with the additional objects and advantages thereof, will best be understood from the following description of exemplary embodiments when read in connection with the accompanying drawings.

DETAILED DESCRIPTION OF THE INVENTION

Figure 1:
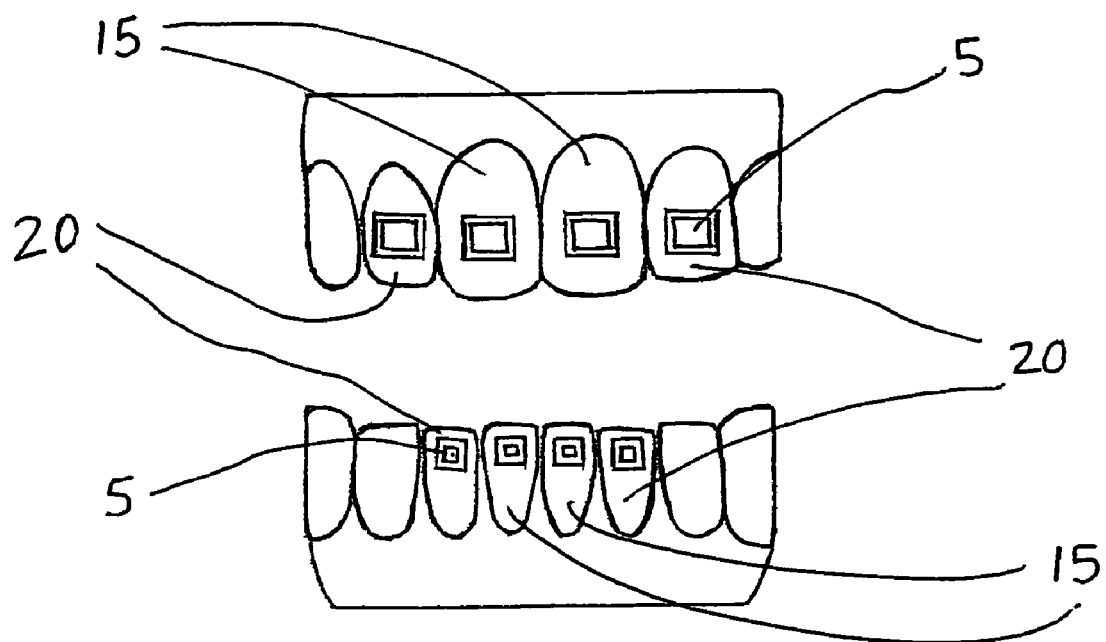
FIG. 1 is a front view of visually simulated tooth brace indicia attached to teeth.

FIG. 1 shows a plurality of individual nonfunctional tooth brace indicia 5 applied to a consumer's teeth. A consumer can choose to cover simply the four central incisors 15 or can additionally cover the lateral incisor teeth 20.

Figure 2:
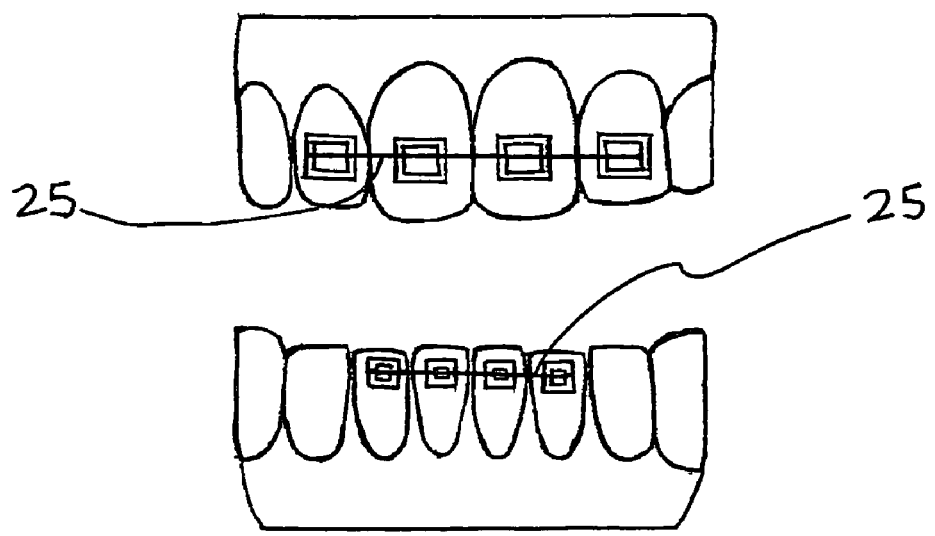
FIG. 2 is a front view of visually simulated tooth brace indicia with a connecting band attached.

FIG. 2 shows a plurality of individual nonfunctional tooth brace indicia 5 with a connected band 25 linking the individual tooth brace indicia. The connecting band can connect the top and bottom sets of either two or four tooth brace indicia.

Figure 3:
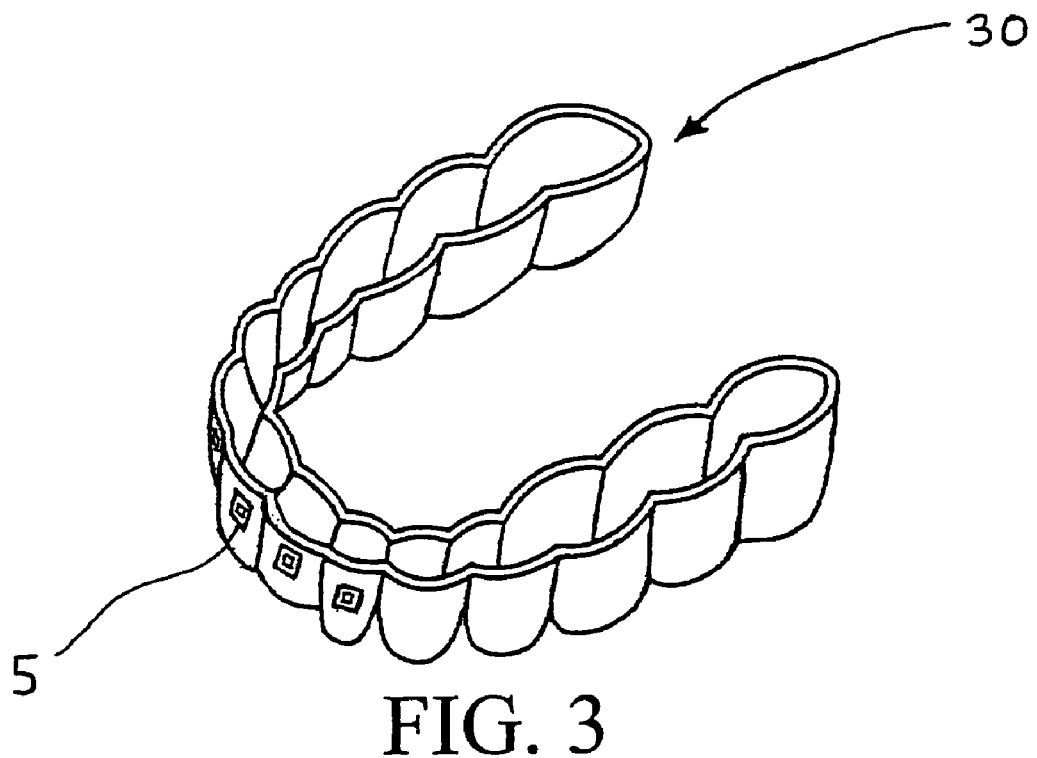
FIG. 3 is a perspective view of a clear plastic tooth mold with inset tooth brace indicia.

FIG. 3 shows a clear plastic tooth mold 30 with a plurality of tooth brace indicia inset. The clear plastic mold can be form fitted to a consumer's teeth much like that of an athletic mouth guard and slips over the teeth in a removable fashion.

Figure 4:
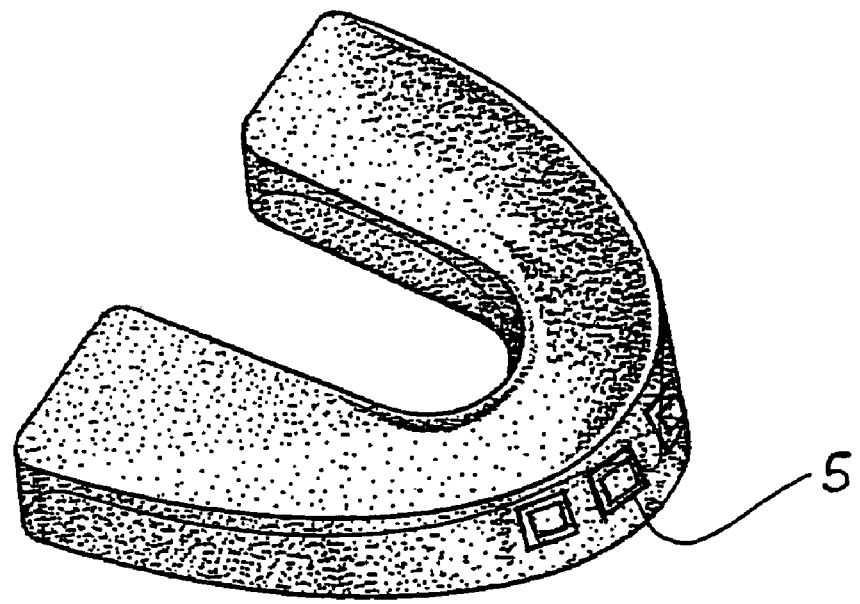
FIG. 4 is a perspective view of a U-shaped self-molding material with laminated tooth brace indicia.

FIG. 4 shows a U-shaped clear self-molding material with a plurality of tooth brace indicia laminated with the self-molding material.

A first embodiment of the present invention is generally shown in FIG. 1. It is envisioned that the consumer, upon selecting the number of tooth brace indicia 5 desired, will attach the individual nonfunctional tooth brace indicia 5 on each desired tooth (15, 20) using FDA approved adhesive. The visual tooth brace indicia 5 can be letters of the alphabet, numbers, and other symbols or any combination thereof. The FDA approved adhesive, such as Dermabond skin glue, can be made as a contact adhesive or as a wettable adhesive so that the consumer either applies the indicia 5 directly or wets them prior to application. The user can remove the indicia 5 by using excess amounts of water and swirling it in their mouth while applying tongue pressure. If the indicia 5 are the sugar-free candied version, the consumer can simply wait until the indicia 5 dissolve to remove them.

In a second embodiment of the present invention, as show in FIG. 2, the same individual nonfunctional tooth brace indicia 5 are used but are attached to one another by a connecting band 25. The connecting band 25 can simulate wire as in functioning tooth adjusting braces. The consumer, upon selecting the number of tooth brace indicia 5 desired, will attach the braces by applying to the teeth (15, 20) in a formable manner. The consistency of the brace material is such that as the consumer applies the braces to the teeth (15, 20), the braces will flex in a manner so that the attachment to all the desired teeth (15, 20) can be made. The braces can be attached in the same manner using the same FDA approved adhesive as in the first embodiment. The user can remove the braces by using excess amounts of water and swirling it in their mouth while applying tongue pressure. If the braces are the sugar-free candied version, the consumer can simply wait until the braces dissolve to remove them.

A third embodiment according to the present invention is shown in FIG. 3. A formable plastic mouthpiece 30 can be used to mold the desired tooth shape and form a cap to cover the teeth in much the same fashion as an athletic mouthguard. The individual nonfunctional tooth brace indicia 5 are embedded into the plastic between the teeth and the lips of the consumer so that the indicia 5 are visible as the consumer reveals their teeth. The mouthpiece 30 containing the tooth brace indicia 5 can either be removable or can be glued using the FDA approved glue as in embodiments one and two.

A fourth embodiment according to the present invention is shown in FIG. 4. Braces are laminated in a U-shaped clear self-molding material such as silicone. In this manner the U-shaped self-molding material can be custom fit to the user's teeth and attached with an FDA approved glue as in embodiments one, two, and three. The self-molding material can be white to match the teeth or any other color or any combination of colors.

It is clear that the present invention in all of its embodiments can be uniformly or diversely colored, including but not limited to silver, black, yellow, or red. The individual tooth brace indicia 5 can be colored differently than the connecting band allowing for a myriad color combination of choices, allowing the consumer to express him or herself as seen fit.

Additionally, it is also clear that the present invention in embodiments one and two can be adapted to cover any number of top or bottom teeth. For example, a user could choose to cover six top or bottom teeth in a symmetrical fashion.

This invention has been described with reference to the preferred embodiments, obvious modifications and alterations will occur to others upon reading and understanding the proceeding detailed description. It is intended that the invention be construed as including all such modifications and alterations.

The invention claimed is:

1. Visually simulated braces, comprising:
   a plurality of individual nonfunctional tooth brace visual indicia; and
   a digestible adhesive applied to the tooth brace visual indicia,
   wherein the individual nonfunctional tooth brace visual indicia are edible.

2. The visually simulated braces of claim 1, wherein the nonfunctional tooth brace visual indicia are silver in color.

3. The visually simulated braces of claim 1, wherein the braces cover four central incisor teeth.

4. The visually simulated braces of claim 1, wherein the braces cover four central incisor teeth and four lateral incisor teeth.

5. The visually simulated braces of claim 1, wherein the digestible adhesive will allow the braces to remain adhered to the teeth for up to four hours.

6. The visually simulated braces of claim 1, wherein the digestible adhesive will allow the braces to remain adhered to the teeth for up to 12 hours.

7. Visually simulated braces, comprising:
   a plurality of individual nonfunctional tooth brace visual indicia;
   a connecting band connecting each of the individual nonfunctional tooth brace indicia; and
   a digestible adhesive applied to the tooth brace visual indicia;
   wherein the individual nonfunctional tooth brace visual indicia are edible.

8. The visually simulated braces of claim 7, wherein the connecting band resembles a wire.

9. The visually simulated braces of claim 7, wherein the nonfunctional tooth brace visual indicia are silver in color.

10. The visually simulated braces of claim 7, wherein the braces cover four central incisor teeth.

11. The visually simulated braces of claim 7, wherein the braces cover four central incisor teeth and four lateral incisor teeth.

12. The visually simulated braces of claim 7, wherein the digestible adhesive will allow the braces to remain adhered to the teeth for up to four hours.

13. The visually simulated braces of claim 7, wherein the digestible adhesive will allow the braces to remain adhered to the teeth for up to 12 hours.

14. Visually simulated braces comprising:
    a clear formable plastic fitted to an individual's teeth; and
    individual nonfunctional visual tooth brace indicia imbedded into the plastic wherein the individual nonfunctional visual tooth brace indicia are visible through the plastic.

15. The visually simulated braces of claim 14, wherein the individual nonfunctional tooth visual tooth brace indicia are edible.

16. The visually simulated braces of claim 14, wherein the tooth brace visual indicia are silver in color.

17. The visually simulated braces of claim 14, wherein the individual visual tooth brace indicia are viewable over four central incisor teeth.

18. The visually simulated braces of claim 14, wherein the individual visual tooth brace indicia are viewable over four central incisor teeth and four lateral incisor teeth.

19. The visually simulated braces of claim 14, wherein addition of a digestible adhesive will allow the braces to remain adhered to the teeth for up to four hours.

20. The visually simulated braces of claim 14, wherein addition of a digestible adhesive will allow the braces to remain adhered to the teeth for up to 12 hours.

21. The visually simulated braces of claim 14, wherein the braces are removable and reusable.

22. The visually simulated braces of claim 14, wherein the individual nonfunctional visual tooth brace indicia are connected by a band.

\* \* \* \* \*